US008692020B2

(12) United States Patent
Jung et al.

(10) Patent No.: US 8,692,020 B2
(45) Date of Patent: Apr. 8, 2014

(54) ORGANIC FRAMEWORK

(75) Inventors: Dong Hyun Jung, Daejeon (KR);
Minkyoung Kim, Gyeonggi-do (KR);
Daejin Kim, Seoul (KR); Seung-Hoon Choi, Seongnam-si (KR); Jihye Yoon, Gyeongsangnam-do (KR); Sang Beom Choi, Gyeonggi-do (KR); Eunhee Jo, Nowon-gu Seoul (KR); Jaheon Kim, Gyeonggi-do (KR)

(73) Assignee: Insilicotech Co., Ltd (KR)

( * ) Notice: Subject to any disclaimer, the term of this patent is extended or adjusted under 35 U.S.C. 154(b) by 387 days.

(21) Appl. No.: 13/129,515

(22) PCT Filed: Nov. 17, 2009

(86) PCT No.: PCT/KR2009/006769
§ 371 (c)(1),
(2), (4) Date: May 16, 2011

(87) PCT Pub. No.: WO2010/056092
PCT Pub. Date: May 20, 2010

(65) Prior Publication Data
US 2011/0230678 A1     Sep. 22, 2011

(30) Foreign Application Priority Data

Nov. 17, 2008  (KR) .................. 10-2008-0114056

(51) Int. Cl.
*C07C 5/02*       (2006.01)
(52) U.S. Cl.
USPC ............................................... 564/11
(58) Field of Classification Search
USPC ............................................... 564/11
See application file for complete search history.

(56) References Cited

U.S. PATENT DOCUMENTS

2006/0154807 A1*  7/2006  Yaghi et al. .................. 502/150

FOREIGN PATENT DOCUMENTS

KR    10-2008-0064077 A    7/2008

OTHER PUBLICATIONS

Nikolas A. A. Zwaneveld et al., 'Organized Formation of 2D Extended Covalent Organic Frameworks at Surfaces', J. Am. Chem. Soc., 2008, 130, 6678-6679, Publication Date (Web) : Apr. 30, 2008. See p. 6678.
Adrien P. Cote et al., 'Porous, Crystalline, Covalent Organic Frameworks', Science Nov. 18, 2005. vol. 310. No. 5751, pp. 1166-1170. See p. 1167.
Adrien P. Cote et al., 'Reticular Synthesis of Microporous and Mesoporous 2D Covalent Organic Frameworks', J. Am. Chem. Soc., 2007, 129 (43), pp. 12914-12915. See p. 12914.
International Search Report for International Application No. PCT/KR2009/006769 dated Jun. 16, 2010 with English translation.

* cited by examiner

*Primary Examiner* — Johann R Richter
*Assistant Examiner* — Kofi Adzamli
(74) *Attorney, Agent, or Firm* — Cantor Colburn LLP

(57) ABSTRACT

Disclosed is an organic framework including: planar layers formed by successively connecting building blocks arranged in the vicinity of each other, in which each of the building blocks includes two or three $C_6$ to $C_{204}$ aromatic ring groups covalently bonded to a linear or annular boron-containing cluster; and a Lewis base coordinated to the boron-containing cluster within the planar layers.

21 Claims, 6 Drawing Sheets ically adsorbed on the surface of the materials with a very low
ORGANIC FRAMEWORK This is a U.S. national stage application of International Application No. PCT/KR2009/006769, filed on 17 Nov. 2009. Priority under 35 U.S.C. 119(a) and 35 U.S.C. 365(b) is claimed from Japanese Application No. KR 10-2008-0114056, filed 17 Nov. 2008, the disclosure of which is also incorporated herein by reference.

TECHNICAL FIELD

The present invention relates to an organic framework capable of adsorbing/desorbing and/or storing gas or organic molecules.

BACKGROUND ART

Fossil fuels occupying 90% or more of currently used energy demand cannot be recycled, and their reserves are limited. The fossil fuels, when used, pollute the environment by emitting air pollutants such as $NO_x$, $SO_x$, dust. Also, an increase in the atmosphere concentration of carbon dioxide emitted by the combustion of fossil fuels has recently raised anxiety about global warming.

As a new energy carrier for substituting for such a fossil fuel, hydrogen, which has been widely used as a raw material of a chemical product, and a process gas of a chemical process, is spotlighted. Hydrogen has advantages as described below. First, hydrogen, when used as a raw material, does not generate a pollutant except for a trace of $NO_x$ through combustion. Thus, it is easy to use hydrogen as a fuel for direct combustion or a fuel for a fuel cell. Second, hydrogen can be easily produced as a gas or a liquid, and can easily be stored in various forms such as high-pressure gas, liquid hydrogen, metal hybride, or the like. Third, hydrogen can be produced in a large amount from water. Also, hydrogen, even after being used, is recycled as water, thereby eliminating anxiety about the exhaustion of natural resources. Fourth, hydrogen can be used in almost all fields, currently using an energy system, such as industrial elementary materials, general fuels, hydrogen fueled automobiles, hydrogen fueled aircrafts, fuel cells, or the like.

However, in order to use hydrogen, there is required a medium capable of easily storing a large amount of hydrogen. Accordingly, in order to develop a hydrogen storage medium, researches on a hydrogen storage alloy, a carbon nanotube, a zeolite, or the like have been recently in progress. However, in a case of the hydrogen storage alloy, since a stored material is chemically bonded to a hydrogen molecule with a very high binding energy, there is a problem in that there is required another energy for releasing the bonded hydrogen. Also, unlike the hydrogen storage alloy, in a case of the carbon nanotube, or the zeolite, since hydrogen molecules are physically adsorbed on the surface of the materials with a very low binding energy, there is a problem in that storage capacity of hydrogen at room temperature•atmospheric pressure is very low.

Professor Yaghi's research team of the University of California, Berkeley has recently reported on a covalent organic framework (COF) (US 2006/0154807 A1). The COF is a material formed through a covalent bond between only atoms (such as hydrogen, boron, carbon, nitrogen, oxygen, etc.), and may be formed by a condensation reaction of benzene diboronic acid (BDBA). Such a COF has not only a rigid micro-(or meso-)porous structure, but also a high thermal stability, and a low density. Also, it has a specific surface area higher than some conventionally known materials such as zeolite, porous silicates, etc.

Accordingly, researches on the use of such a COF as a new hydrogen storage medium are in progress.

DISCLOSURE

Technical Problem

The inventors of the present invention found that in the case of 2D covalent organic frameworks in which planar layers are sequentially stacked, hydrogen can be inserted into pores, but cannot be easily inserted between layers due to a very narrow interlayer distance of the planar layers.

Therefore, the present invention has found that when a Lewis base is introduced into the planar layers formed by successively connecting building blocks which comprises a linear or annular boron-containing cluster, and two or three $C_6$ to $C_{204}$ aromatic ring groups, the interlayer distance of the planar layers is appropriately widened, and thus, the interlayer spaces can be valid for the hydrogen storage.

It is an object of the present invention to provide an organic framework which can adsorb hydrogen in a larger amount.

Technical Solution

In accordance with an aspect of the present invention, there is provided an organic framework including: a plurality of planar layers formed by successive connections between building blocks, in which each of the building blocks includes two or three $C_6$ to $C_{204}$ aromatic ring groups bonded to a linear or annular boron-containing cluster; and a Lewis base coordinated to the boron-containing cluster within the planar layers.

Also, the present invention provides an adsorbent, and a catalyst, which include the above described organic framework.

Advantageous Effects

In the organic framework according to the present invention, a Lewis base is coordinated to a linear or annular boron-containing cluster of planar layers formed by successively connecting building blocks arranged in the vicinity of each other, in which each of the building blocks includes two or three $C_6$ to $C_{204}$ aromatic ring groups, and the boron-containing cluster. Accordingly, the interlayer distance between the planar layers is widened by the Lewis base coordinated to the planar layers, thereby allowing a large amount of hydrogen to be inserted into the layers. Thus, it is possible to adsorb a large amount of hydrogen.

Also, due to the Lewis base bonded to the planar layers, the organic framework according to the present invention can irreversibly or reversibly adsorb hydrogen, and thus can be used as a hydrogen storage medium having high storage capability.

MODE FOR INVENTION

Hereinafter, the present invention will be described in detail.

In the present invention, a "linear or annular boron-containing cluster" means a linear or annular molecule containing boron, in which atoms other than boron are covalently bonded to two reaction sites among available reaction sites of the boron.

Also, in the present invention, an aromatic ring group means not only an aromatic cyclic hydrocarbon, a heterocyclic aromatic compound, and a polycyclic aromatic compound, but also a fused ring and a connected form, which are made of two or more rings among the above mentioned aromatic rings.

In general, a covalent organic framework (COF) indicates a porous material formed through a covalent bond between atoms such as hydrogen, boron, carbon, nitrogen, oxygen, etc. For example, a conventionally known COF is a material formed through covalent bonds between building blocks, in which each of the building blocks includes a linear or annular boron-containing cluster, and an aromatic ring group.

Specifically, the COF has a network structure, in which the linear or annular boron-containing cluster is covalently bonded to same or different two or three aromatic ring groups (ex. a phenylene group, etc.), and the covalently bonded aromatic ring groups are covalently bonded and connected to other one or more linear or annular boron-containing clusters in a chain-like manner. Herein, the linear or annular boron-containing cluster is formed through a covalent bond between a boron atom and an atom (such as oxygen or nitrogen) selected from groups 15 and 16 of the Periodic Table.

More specifically, an aromatic ring group constituting one building block (first building block) may be covalently bonded not only to a linear or annular boron-containing cluster constituting the first building block, but also to another linear or annular boron-containing cluster constituting another adjacent building block (second building block), and also, the linear or annular boron-containing cluster of the second building block may be covalently bonded to an aromatic ring group of a further building block (third building block), in a chain-like manner.

The COF formed as described above has a rigid porous structure with a low density and a high thermal stability.

Figure 3:
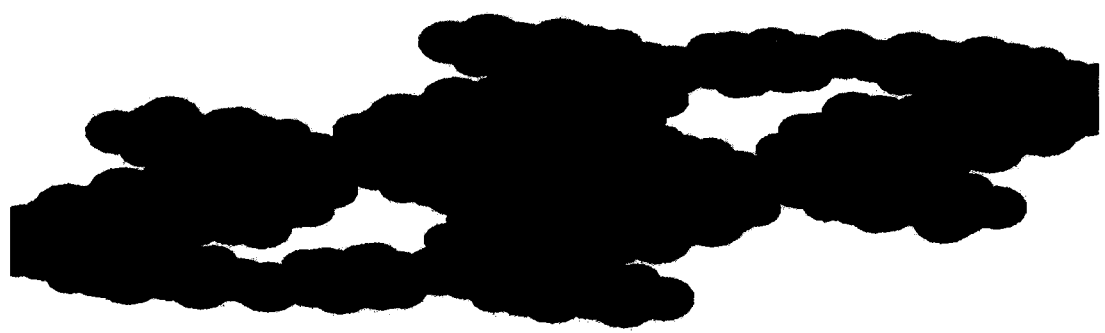
FIG. 3 shows a view three-dimensionally illustrating a conventionally known organic framework (COF-1).

Herein, conventionally known COFs include a COF having a two-dimensional planar network structure (hereinafter, referred to as a 'two-dimensional COF') such as COF-1 [$(C_3H_2BO)_6 \cdot (C_9H_{12})_1$], COF-5 [$C_9H_4BO_2$], or the like. Specifically, unlike another COF (hereinafter, referred to as a 'three-dimensional COF'), the two-dimensional COF has planar layers formed by successively connecting building blocks, in which each of the building blocks includes a linear or annular boron-containing cluster, and $C_6$ to $C_{204}$ aromatic ring groups. Due to the interaction between such planar layers, the two-dimensional COF has a dense layer structure with planar layers (see FIG. 3).

Such a two-dimensional COF has a high binding energy with hydrogen, compared to a three-dimensional COF, but can adsorb only a small amount of hydrogen due to the small surface area capable of adsorbing hydrogen.

Figure 4:
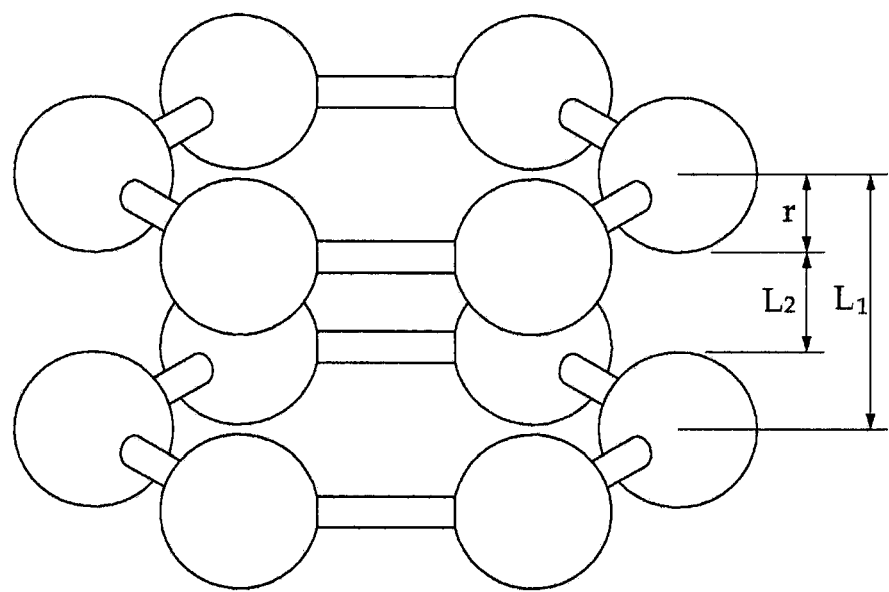
FIG. 4 shows a view illustrating an interlayer distance between planar layers within an organic framework according to the present invention.

Especially, in the case of the two-dimensional COF having the layered structure, the size of pores formed within the COF is large enough to allow a molecule larger than hydrogen gas to pass through, while the distance between the planar layers is very narrow due to interaction between the planar layers. For example, in the case of COF-1, the size of pores formed within the COF-1 is about 15 Å, while an interlayer distance [a distance between centers of atoms (e.g. boron, carbon, etc.) forming respective layer planes] ($L_1$) is about 3 Å (see FIG. 4). However, herein, in consideration of Van der Waals radius (r) of atoms forming planes of respective layers, an interlayer distance ($L_2$) is actually less than 3 Å. Thus, hydrogen gas (hydrogen molecules) having a kinetic diameter of about 2.89 Å cannot be easily inserted between layers. Accordingly, when the two-dimensional COF is used to adsorb/store hydrogen, the hydrogen can be inserted into pores, but cannot be easily inserted between layers.

For this reason, the two-dimensional COF can adsorb a small amount of hydrogen, compared to the three-dimensional COF. Furthermore, although the two-dimensional COF has a specific surface area higher than zeolite or porous silicates which have been conventionally used as a hydrogen storage medium, it can adsorb only a small amount of hydrogen. In addition, the two-dimensional COF has a problem in that it shows a low efficiency as a hydrogen storage medium, because the adsorption of hydrogen is physical adsorption, and thus the hydrogen adsorbed on the COF can be desorbed due to a change in temperature or pressure.

In the art, it is expected that when graphite, a kind of layered compound, is used to adsorb hydrogen, about 6 Å of an interlayer distance of the graphite allows the largest amount of hydrogen to be adsorbed.

Therefore, in the present invention, in order to widen the distance between planar layers within the two-dimensional COF, a Lewis base is used to increase the interlayer distance and at the same time increase an interactive force with a guest molecule such as hydrogen. The Lewis base is coordinated to a linear or annular boron-containing cluster within the planar layers, thereby allowing the guest molecule to be inserted not only into pores but also between planar layers. This improves adsorption of guest molecules.

Specifically, the organic framework according to the present invention has planar layers formed by covalent bonds between adjacent different building blocks, in which each of the building blocks includes a linear or annular boron-containing cluster covalently bonded to same or different two or three $C_6$ to $C_{204}$ aromatic ring groups. A boron atom of the linear or annular boron-containing cluster within each of the planar layers is coordinated to a Lewis base. Herein, the boron atom may be coordinated to the Lewis base in the vertical direction of the planar layers.

Due to the Lewis base coordinated to each of the planar layers, the distance between a planar layer and its adjacent planar layer becomes up to about 4 to 15 Å, which is wider than an interlayer distance of a conventionally known two-dimensional COF. Such an interlayer distance of about 4 to 15 Å allows hydrogen to be easily inserted between layers as well as pores formed within the organic framework. Thus, on the organic framework of the present invention, a large amount of hydrogen can be adsorbed. Also, the organic framework of the present invention has a specific surface area of 300 m$^2$/g to 2300 m$^2$/g, and thus can adsorb/store a large amount of hydrogen.

Furthermore, an empty space existing between planar layers is regularly or irregularly partitioned by Lewis bases regularly or irregularly coordinated to the planar layers in the vertical direction of the planar layers, thereby forming a plurality of compartment spaces between the planar layers. The compartment spaces formed as described above may be spaces (or sites) in which hydrogen inserted into the organic framework can be adsorbed and stored. Herein, the hydrogen adsorbed on the compartment spaces is physically adsorbed in the same manner as a conventionally known COF. However, in the present invention, the kind of a Lewis base coordinated to the planar layers is appropriately selected. Thus, unlike the conventionally known COF, although the hydrogen is physically adsorbed, it is possible to inhibit the adsorbed hydrogen from being desorbed regardless of a change in temperature or pressure. In other words, the organic framework of the present invention can irreversibly adsorb hydrogen. For this reason, the organic framework of the present invention may be used as a storage medium having high storage capability.

In the organic framework of the present invention, the linear or annular boron-containing cluster may be formed by bonding two atoms (ex. N, P, O, S, etc.) selected from groups 15 and 16 of the Periodic Table, respectively, to two reaction sites among available reaction sites of the boron. Herein, the two atoms bonded to the reaction sites of the boron may be the same or different. Since the boron atom can accept an electron pair, a Lewis base having a lone electron pair is coordinated to the boron atom, and thus, it may increase the interlayer distance. Herein, the Lewis base may be coordinated to the boron atom in the vertical direction of the planar layers.

The linear or annular boron-containing cluster may be represented by Formula 1 or 2 below.

[Formula 1]

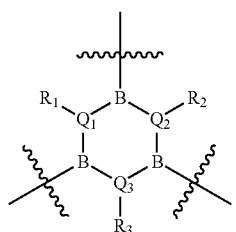

[Formula 2]

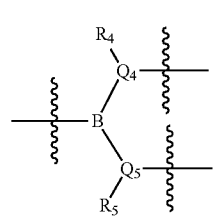

In Formula 1, and Formula 2, each of $Q_1$ to $Q_5$ independently represents an atom selected from groups 15 and 16 of the Periodic Table; each of $R_1$ to $R_5$ independently represents hydrogen, a $C_1$ to $C_{12}$ alkyl group, a $C_6$ to $C_{12}$ aryl group, or halogen. If at least one of $Q_1$ to $Q_5$ is an atom selected from group 16, at least one of $R_1$ to $R_5$ bonded to the corresponding atom of group 16 does not exist.

Examples of a linear or annular boron-containing cluster represented by Formulas 1 and 2 include

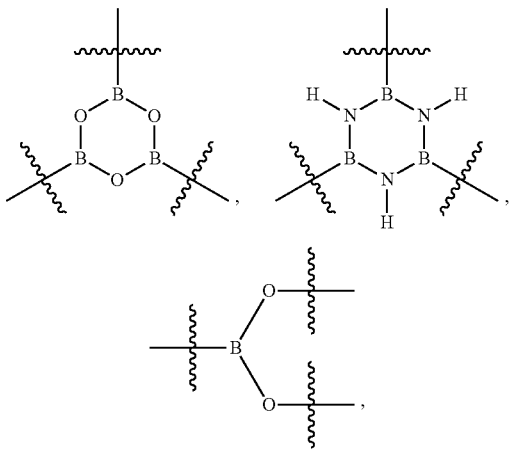

etc., but the present invention is not limited thereto.

The linear or annular boron-containing cluster of the present invention is covalently bonded to same or different two or three $C_6$ to $C_{204}$ aromatic ring groups so as to form a building block.

The $C_6$ to $C_{204}$ aromatic ring group may be represented by any one of Formulas 3, 4, 5, and 6 below, but the present invention is not limited thereto.

[Formula 3]

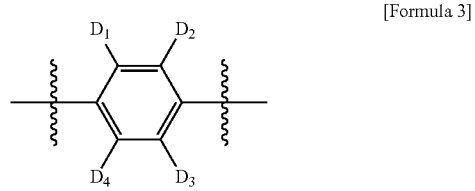

[Formula 4]

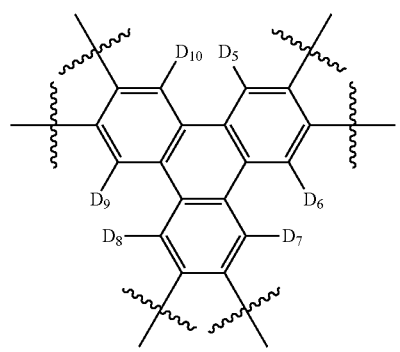

[Formula 5]

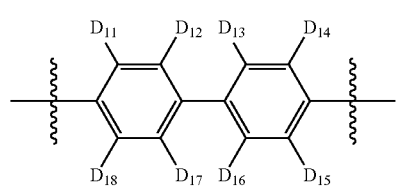

[Formula 6]

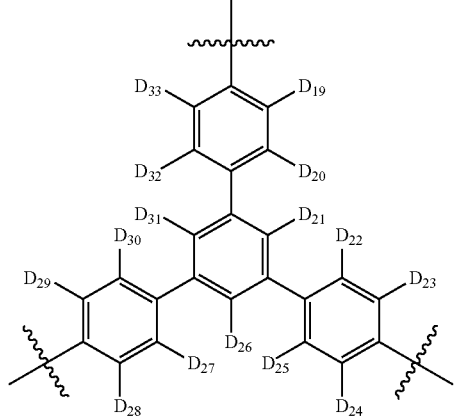

In Formulas 3, 4, 5 and 6, each of $D_1$ to $D_{33}$ may be independently selected from the group consisting of hydrogen, a $C_1$ to $C_{12}$ alkyl group, a $C_6$ to $C_{12}$ aryl group, and halogen.

Non-limiting examples of the $C_6$ to $C_{204}$ aromatic ring group represented by the Formulas include

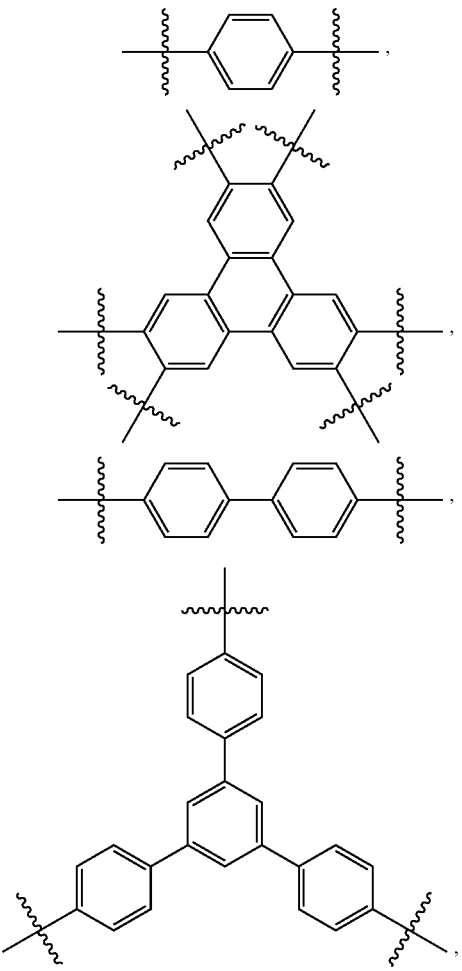

etc.

The above described linear or annular boron-containing cluster may be covalently bonded to same or different two or three $C_6$ to $C_{204}$ aromatic ring groups so as to form various types of building blocks.

If one cyclic boron-containing cluster represented by Formula 1 is covalently bonded to three $C_6$ to $C_{204}$ aromatic ring groups represented by Formula 3, a building block represented by Formula 7 below may be formed.

[Formula 7]

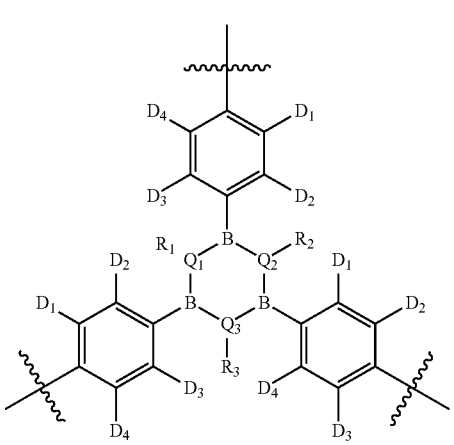

In Formula 7, $Q_1$ to $Q_3$, and $R_1$ to $R_3$ are the same as defined in Formula 1; and $D_1$ to $D_4$ are the same as defined in Formula 3.

Examples of the building block represented by Formula 7 may include building blocks represented by Formulas 7a and 7b below, but the present invention is not limited thereto.

[Formula 7a]

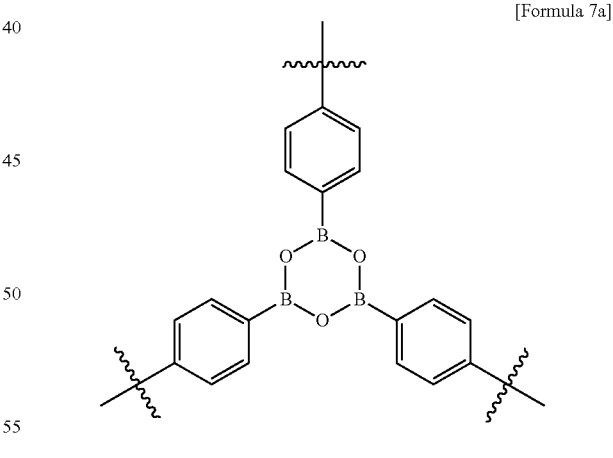

[Formula 7b]

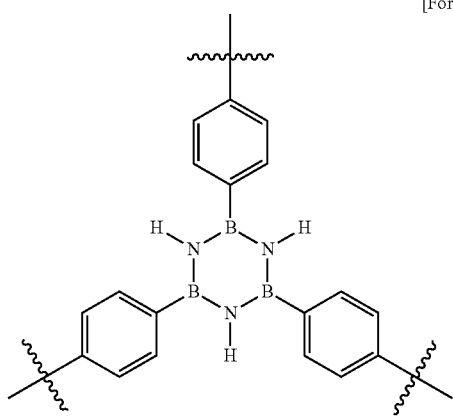

Also, if three linear boron-containing clusters represented by Formula 2 are covalently bonded to three $C_6$ to $C_{204}$ aromatic ring groups represented by Formula 3, and one $C_6$ to $C_{204}$ aromatic ring group represented by Formula 4, a building block represented by Formula 8 below may be formed.

[Formula 8]

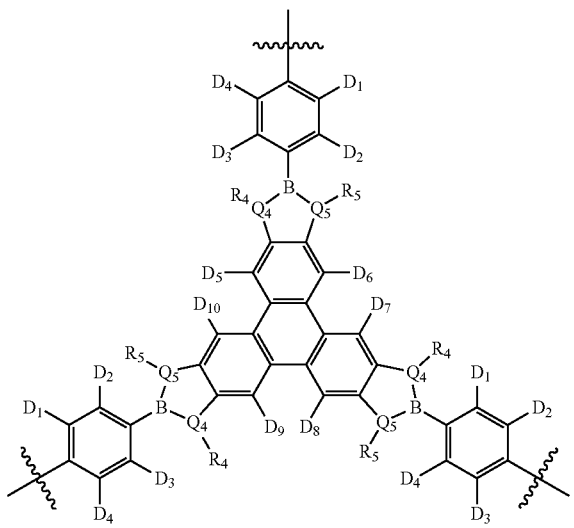

In Formula 8, $Q_4$ to $Q_5$, and $R_4$ to $R_5$ are the same as defined in Formula 2; and $D_1$ to $D_{10}$ are the same as defined in Formulas 3 and 4.

Examples of the building block represented by Formula 8 may include a building block represented by Formula 8a below, but the present invention is not limited thereto.

[Formula 8a]

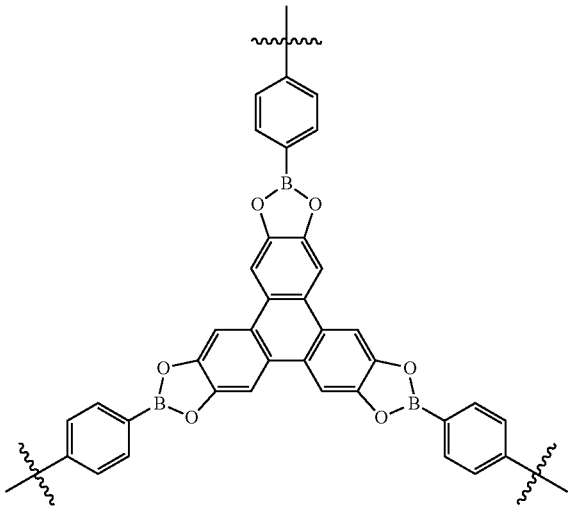

In a planar layer of an organic framework, according to the present invention, a $C_6$ to $C_{204}$ aromatic ring group constituting the building block (first building block) represented by Formula 7 or 8 may be covalently bonded not only to a linear or annular boron-containing cluster constituting the first building block, but also to another linear or annular boron-containing cluster constituting another adjacent building block (second building block) having the same structure as the first building block, and also, the linear boron-containing cluster of the second building block may be covalently bonded to a $C_6$ to $C_{204}$ aromatic ring group of a further building block (third building block) having the same structure as the first building block, in a chain-like manner. The planar layer formed as described above may have various structures.

If the planar layer of the present invention is formed by successive bonds of the building blocks represented Formula 7, the planar layer may be represented by Formula 9 below.

[Formula 9]
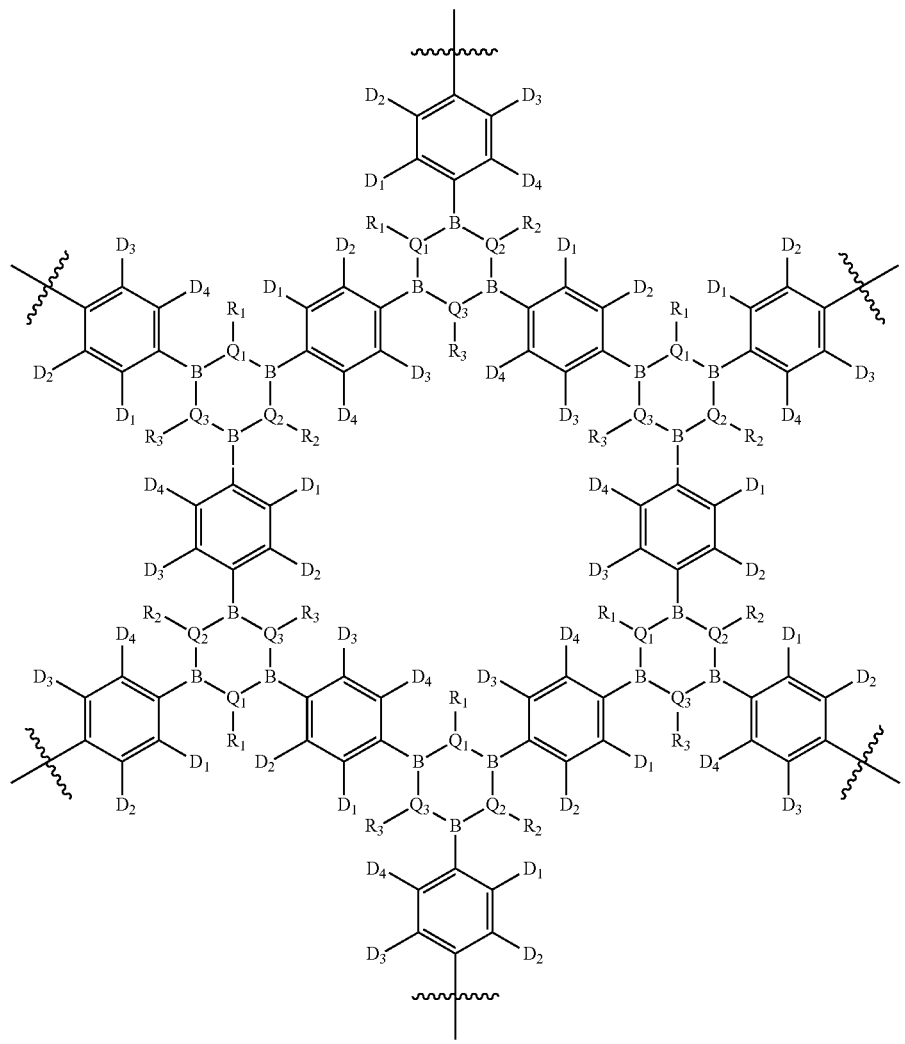
In Formula 9, $Q_1$ to $Q_3$, and $R_1$ to $R_3$ are the same as defined in Formula 1; and $D_1$ to $D_4$ are the same as defined in Formula 3.
Examples of the planar layer represented by Formula 9 may include planar layers represented by Formulas 9a and 9b below, but the present invention is not limited thereto.

[Formula 9a]
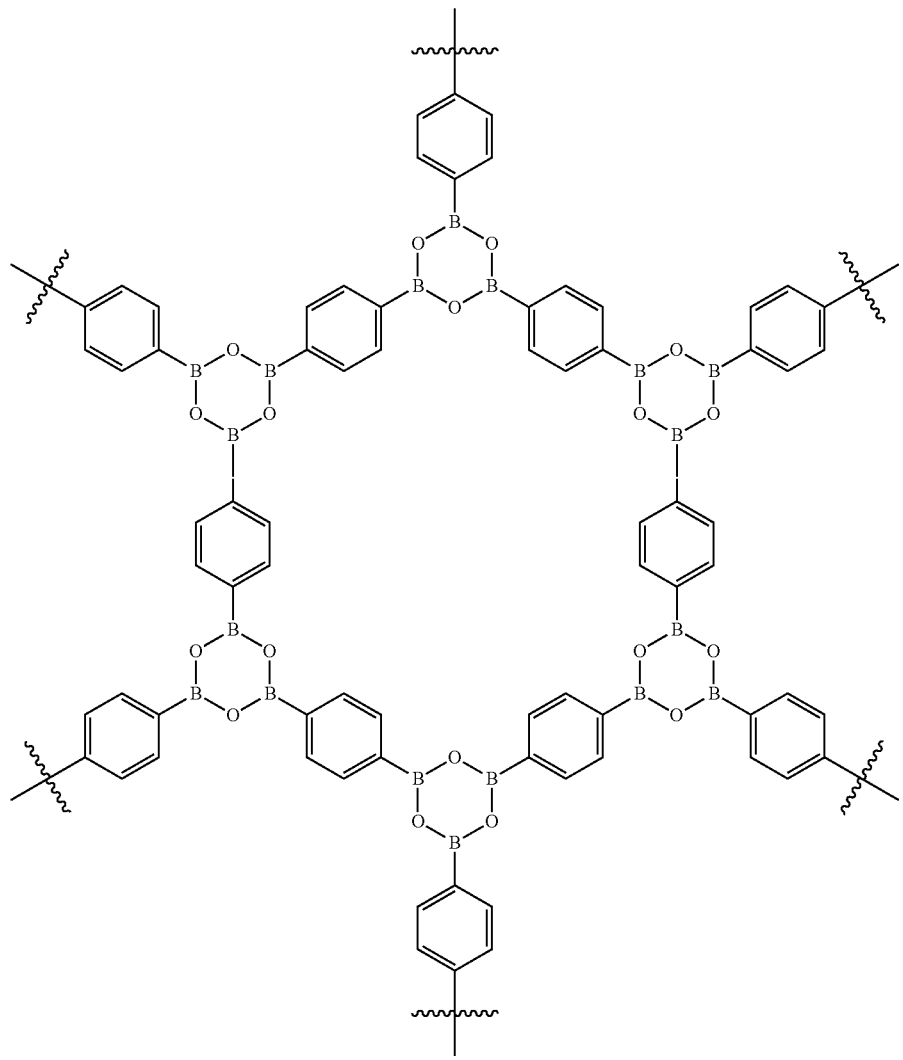
[Formula 9b]
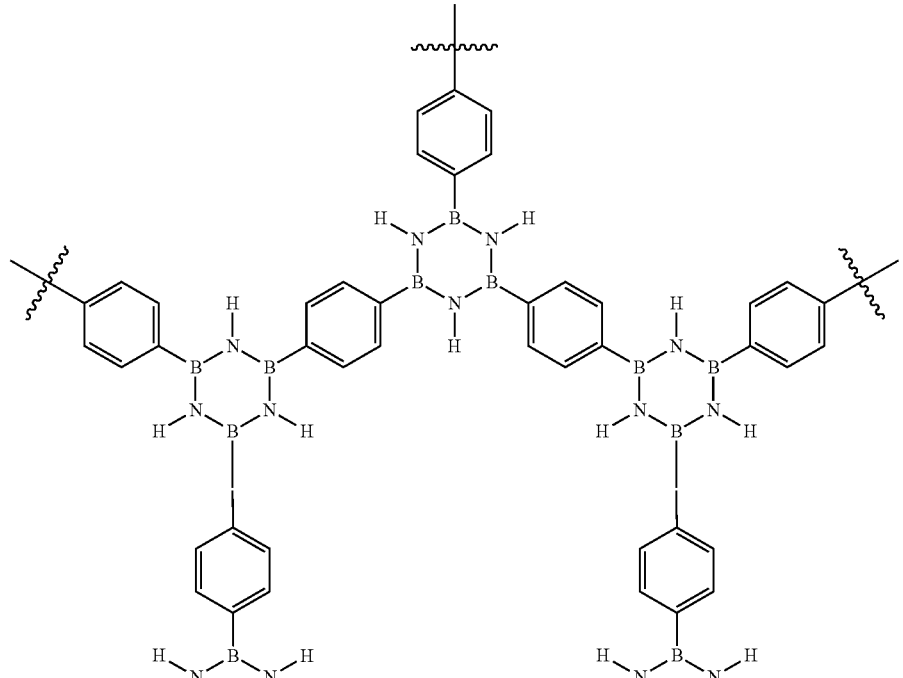

Also, if the planar layer of the present invention is formed by successive bonds of the building blocks represented Formula 8, the planar layer may be represented by Formula 10 below.

Examples of the planar layer represented by Formula 10 may include planar layers represented by Formula 10a below, but the present invention is not limited thereto.

[Formula 10]

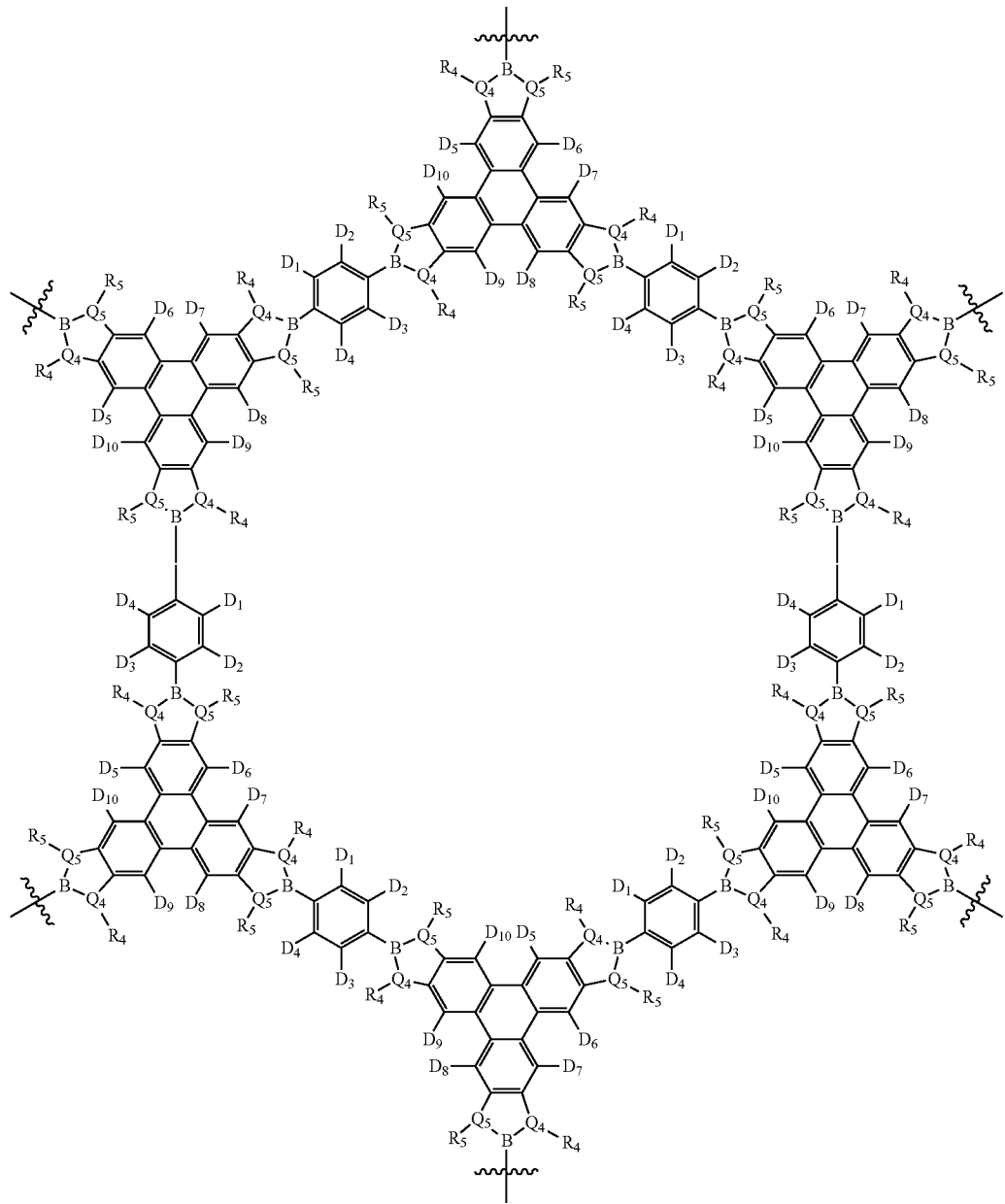

In Formula 10, $Q_4$ and $Q_5$, and $R_4$ and $R_5$ are the same as defined in Formula 2; and $D_1$ to $D_4$ are the same as defined in Formula 3.

[Formula 10a]

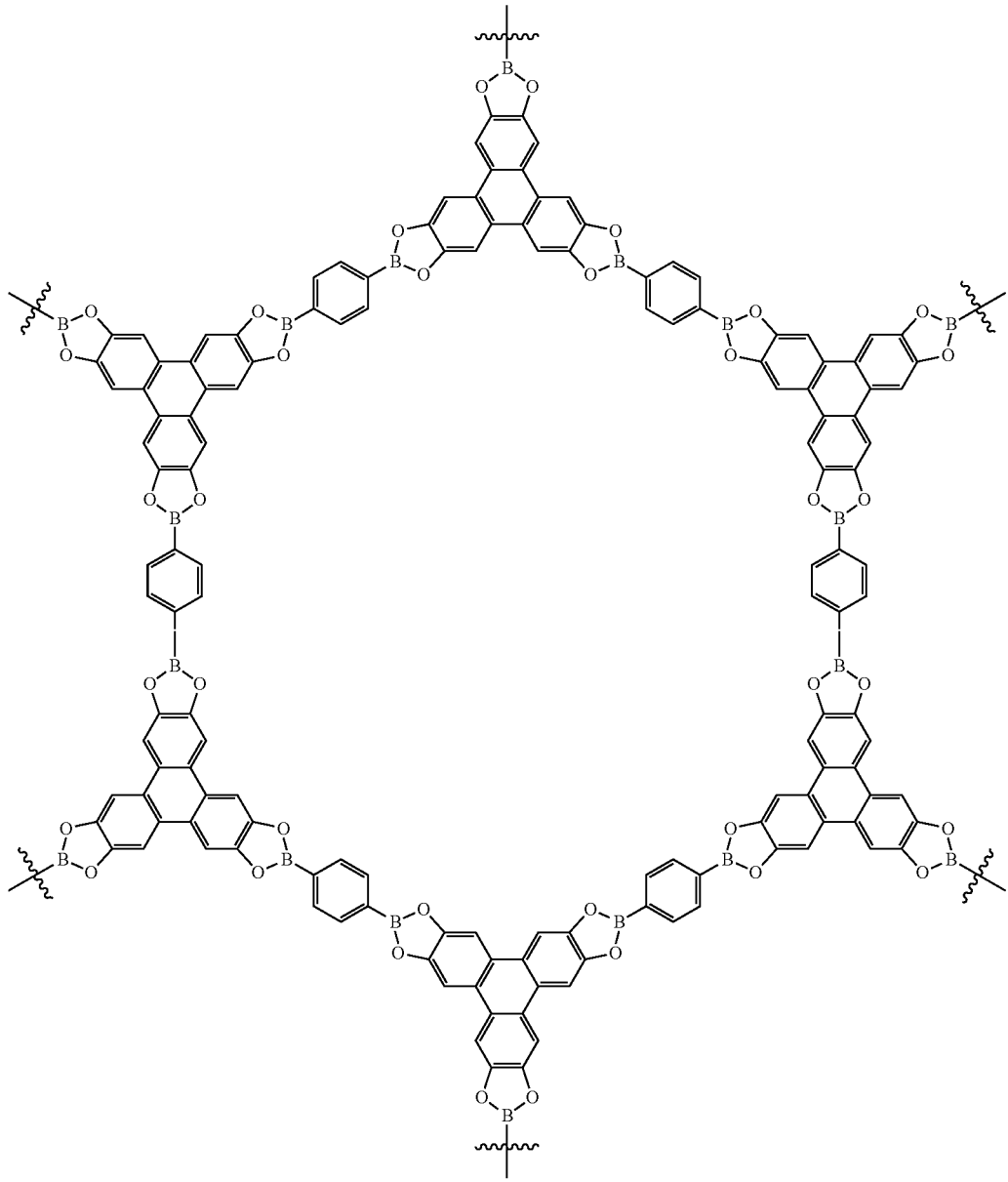

Figure 1:
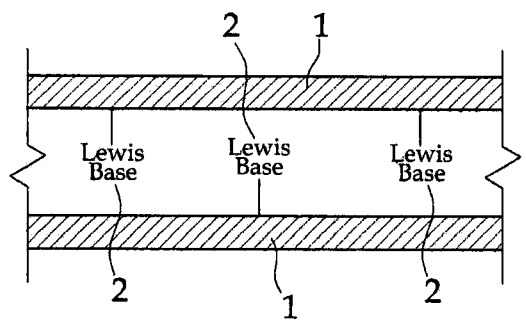
FIG. 1 shows a cross-sectional view schematically illustrating an organic framework of the present invention.
Figure 2:
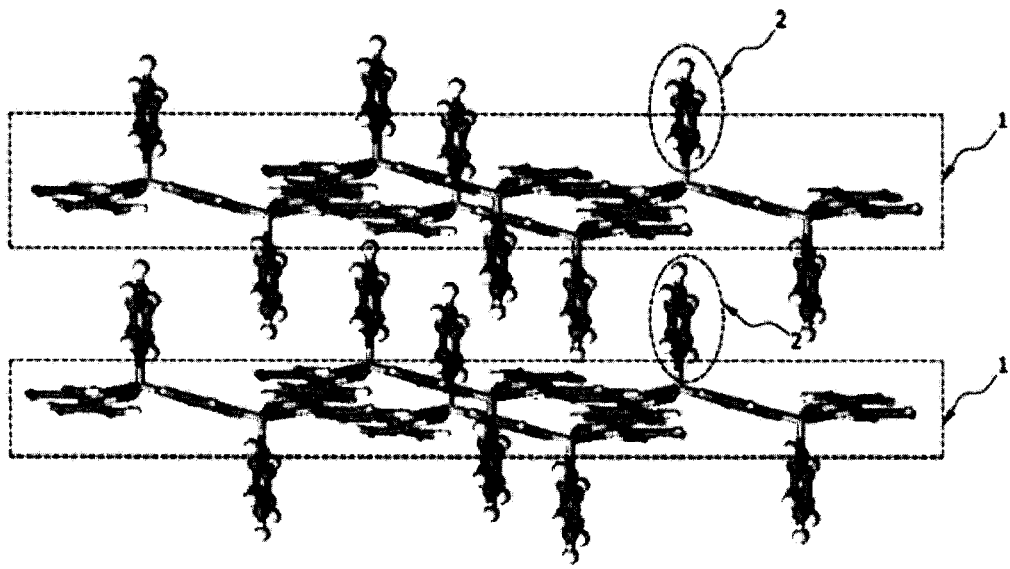
FIG. 2 shows a view three-dimensionally illustrating an organic framework according to one embodiment of the present invention.

The organic framework according to the present invention includes the above described planar layer (1) with a Lewis base (2) coordinated to the linear or annular boron-containing cluster within the planar layers (1). Herein, the Lewis base may be coordinated to the boron atom within the boron-containing cluster in the vertical direction of the planar layers (see FIG. 1). For example, pyridines (2) (as a Lewis base) are coordinated to the planar layers 1 represented by Formula 9a in the vertical direction (see FIG. 2). Thus, the organic framework according to the present invention is different from a conventional two-dimensional COF having only planar layers (see FIG. 3).

Due to the Lewis base coordinated to the planar layers, planar layers have a wider gap (size: about 4 to 15 Å) between the layers than the conventional COFs without the Lewis base. Thus, although van der Waals radius of an atom constituting a planar layer has to be considered, the size of the gap is large enough to allow a hydrogen gas (kinetic diameter: about 2.89 Å) to be inserted. And thus, the hydrogen can be easily inserted through such a gap. Also, an empty space existing between layers is regularly or irregularly partitioned by the Lewis bases, and hydrogen inserted into the organic framework may be adsorbed and stored in such compartment spaces.

There is no limitation in the Lewis base that may be used in the present invention, as long as it is a material capable of donating a lone electron pair. However, it is appropriate that the Lewis base is a compound containing at least one atom selected from groups 14 and 15 of the Periodic Table. For example, the Lewis base may be a heterocyclic compound containing one or more atoms selected from the group consisting of N, P, O and S, but the present invention is not limited thereto.

More specific examples of the Lewis base include pyridine, 4-cyanopyridine, 4-dialkylaminopyridine, 4,4'-bipyridine, pyrazine, pyridazine, pyrimidine, 2-methylpyrazine, pyrazol, imidazole, purine, 7-azaindole, quinoline, isoquinoline, quinoxaline, 1,4-diazabicyclo(2.2.2)octane, quinuclidine, 1,3,5-triazine, hexamethyleneteramine, piperidine, piperazine, pyrrolidine, morpholine, tetrahydrofuran, 1,4-dioxane, 1,8-naphthylene disulfide, etc., but the present invention is not limited thereto.

The organic framework of the present invention may be prepared by the method below, but the present invention is not limited thereto. Herein, the prepared organic framework is semicrystalline or crystalline.

For example, the organic framework may be prepared by a reaction of a boron-containing compound represented by any one of Formulas 11, 12, and 13 below, with a Lewis base, in the presence of a solvent selected from the group consisting of mesitylene, 1,4-dioxane, and a mixture thereof.

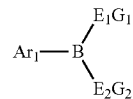

[Formula 11]

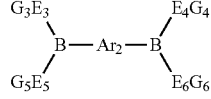

[Formula 12]

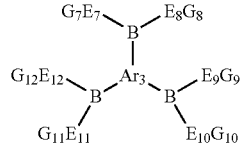

[Formula 13]

In Formulas 11, 12, and 13, $Ar_1$ represents a $C_6$ to $C_{204}$ aryl group, or a $C_6$ to $C_{204}$ heteroaryl group; $Ar_e$ represents a $C_6$ to $C_{204}$ arylene group or a $C_6$ to $C_{204}$ heteroarylene group; $Ar_3$ represents a $C_6$ to $C_{204}$ arenetriyl group or a $C_6$ to $C_{204}$ heteroarenetriyl group; each of $E_1$ to $E_{12}$ independently represents an atom selected from groups 15 and 16 of the Periodic Table; and each of $G_1$ to $G_{12}$ independently represents hydrogen, a $C_1$ to $C_{12}$ alkyl group, a $C_6$ to $C_{12}$ aryl group, or halogen.

According to one example of the present invention, when benzene diboronic acid (BDBA) as the boron-containing compound reacts with pyridine in the presence of mesitylene (as solvent), the planar layers (1) represented by Formula 9A are layered through condensation polymerization between —B—OH site of one BDBA and —B—OH site of another BDBA. Due to the chemical reaction between the BDBA and the pyridine (Lewis base), pyridine (2) is coordinated to a boron atom within the planar layers (1) in the vertical direction of the planar layers. Thus, the organic framework formed according to the present invention can have a widened gap between planar layers, unlike a conventional organic framework (see FIG. 2).

Otherwise, the organic framework may be prepared by a reaction of a boron-containing compound represented by any one of Formulas 11, 12, and 13, with aromatic polyalcohol and a Lewis base, in the presence of a solvent selected from the group consisting of mesitylene, 1,4-dioxane, and a mixture thereof. According to another example of the present invention, when benzene diboronic acid (BDBA) as the boron-containing compound reacts with hexahydroxy triphenylene (HHTP) (as aromatic polyalcohol), and pyridine, in the presence of a mixed solvent of mesitylene and 1,4-dioxane, the planar layers (1) represented by Formula 10a are formed through condensation polymerization between —B—OH site of one BDBA and —B—OH site of another BDBA, and/or —B—OH site of one BDBA and —OH site of one HHTP. Due to the chemical reaction between the BDBA and the pyridine (Lewis base), pyridine (2) is coordinated to a boron atom within the planar layers (1) in the vertical direction of the planar layers. Thus, the organic framework formed according to the present invention can have a widened gap between planar layers, unlike a conventional organic framework.

Specifically, the organic framework of the present invention may prepared by a method comprising: (i) dispersing a boron-containing compound represented by any one of Formulas 11, 12, and 13, in a solvent selected from the group consisting of mesitylene, 1,4-dioxane, and a mixture thereof to form a dispersion (first dispersion); (ii) adding a Lewis base to the first dispersion to form a dispersion (second dispersion); and (iii) heating the second dispersion, but the present invention is not limited thereto. Also, in the above described preparation method, when the first dispersion is formed, aromatic polyalcohol may be further dispersed. Also, the preparation method may further include a step of dispersing the first dispersion by an ultrasonic device after the step of forming the first dispersion.

1) First, in the present invention, the solvent may be used in an amount of about 1 to 3 ml. If the solvent is included in an amount of less than 1 ml, the reaction may not occur due to very low reactivity, and on the other hand, if the solvent is included in an amount of greater than 3 ml, a non-porous polymer may be formed due to high reactivity.

Also, when the solvent is a mixture of mesitylene and 1,4-dioxane, mesitylene and 1,4-dioxane are preferably mixed in a volume ratio of mesitylene: 1,4-dioxane=1:1 to 1:3. If a volume ratio of mesitylene is too high with respect to total volume of the solvent, solubility of a reactant may be significantly reduced. Thus, the reaction may be very slowly carried out or not occur. On the other hand, if a volume ratio of mesitylene is too low with respect to total volume of the solvent, the reaction may be very quickly carried out. Thus, a non-porous polymer or an oligomer, which cannot have a regular framework, may be formed.

Specific examples of the boron-containing compound represented by any one of Formulas 11, 12, and 13, to be dispersed in such a solvent, include benzene diboronic acid (BDBA), biphenyl-4,4'-diboronic acid (BPDA), tolane-4,4'-diboronic acid, stilbene-4,4'-diboronic acid, 1,3,5-benzenetriboronic acid (BTBA), 1,3,5-benzenetris(4-phenylboronic acid)(BTPA), 1,4-phenylenediboranediamine, biphenyl-4,4'-diyldiboranediamine, etc., but the present invention is not limited thereto.

Such a boron-containing compound may be dispersed in a solvent in an amount of about 50 to 250 parts by weight with respect to 100 parts by weight of the solvent. When the boron-containing compound is used in the above mentioned amount, it is possible to further promote the condensation polymerization and to inhibit a non-porous polymer or an oligomer from being formed, in the present invention.

In the present invention, aromatic polyalcohol, together with the boron-containing compound, may be dispersed in the solvent so as to form the first dispersion. The content of the mixed solute of the boron-containing compound and the aromatic polyalcohol is the same as the above mentioned content of the boron-containing compound. Herein, it is appropriate that the boron-containing compound and the aromatic polyalcohol are mixed in a molar ratio of boron-containing compound: aromatic polyalcohol=1:1 to 3:1.

Non-limiting examples of the aromatic polyalcohol that may be used in the present invention include hexahydroxy triphenylene, benzene-1,4-diol, biphenyl-4,4'-diol, etc.

In the present invention, optionally, an ultrasonic device may be used to uniformly disperse the boron-containing compound and the aromatic polyalcohol in the first dispersion. Herein, it is appropriate that the ultrasonic device is used under the condition of ultrasonic frequency of about 40 kHz.

2) Then, a Lewis base is added to the first dispersion so as to form a dispersion (hereinafter, referred to as a 'second dispersion'). Herein, the Lewis base may be added in an amount of about 3 to 10 parts by weight with respect to 100 parts by weight of the solvent. If the Lewis base is included in an amount of less than 3 parts by weight, the reaction may occur in a part of planar layers. On the other hand, if the Lewis base is included in an amount of greater than 10 parts by weight, the coordination of the Lewis base to boron is quickly carried out. Thus, the reaction may occur only on the surface of a produced crystalline or semi-crystalline particle.

3) Next, the formed second dispersion is heated in such a manner that the condensation reaction between the boron-containing compounds, together with the chemical reaction between the boron-containing compound and the Lewis base, can be sufficiently carried out. It is appropriate that the heating temperature ranges from about 40 to 160° C. If the heating temperature of the second dispersion is too low, energy required for the chemical reaction between the boron-containing compound and the Lewis base cannot be supplied. Thus, the reaction may not occur. On the other hand, if the heating temperature is too high, the reaction may be quickly carried out, thereby forming an oligomer. It is appropriate that the heating is performed in a state where the first dispersion is sealed.

The organic framework according to the present invention may be used as an adsorbent capable of adsorbing or storing a large amount of gas or organic materials. Non-limiting examples of the gas include ammonia, carbon dioxide, carbon monoxide, hydrogen, amine, methane, oxygen, argon, nitrogen, etc., and non-limiting examples of the organic material include organic materials having $C_1$ to $C_{12}$, such as methane, ethane, propane, butane, pentane, hexane, cyclo hexane, methanol, ethanol, propanol, isopropanol, benzene, toluene, etc.

Also, the organic framework of the present invention may be used, besides the adsorbent, as a catalyst (including a carrier for a catalyst), a sensor, an isolate, a drying agent, an ion exchange material, a molecular sieve (separator), a material for chromatography, a selective molecule releaser (or adsorbent), a molecule recognizing substance, a nanotube, a nano reactor, etc.

Hereinafter, the present invention will be described in more detail with reference to Examples. However, the following Examples are to illustrate the present invention, but should not be interpreted as limitation thereon.

Example 1

In a 4 ml glass bottle containing 1.0 ml of mesitylene (as a solvent), 25 mg (0.15 mmol) of BDBA (benzene diboronic acid) was added to prepare a dispersion, and then an ultrasonic dispersing device (Ultrasonic frequency: 40 kHz) was used to disperse the dispersion for 1 hour. Then, 0.1 ml of pyridine is added into the dispersion. Next, the glass bottle was sealed, and was heated in an oven at a temperature 85° C. for 3 days to provide white solid powder. The powder was separated through filtration, sufficiently washed with acetone, and dried under a vacuum for about 3 hours or more.

An element analyzer was used to analyze the obtained solid powder. The results of element analysis were as follows.

Element analysis: $(C_3H_2BO)_6$ (mesitylene)$_3$ (pyridine)$_2$=$C_{55}H_{58}N_2O_6B_6$, Calcd. C, 72.76%, H, 6.44%, N, 3.09%. Found. C, 72.77%, H, 6.66%, N, 2.98%.

Example 2

Solid powder was obtained in the same manner as in Example 1 except that a mixture of 0.5 ml of mesitylene and 0.5 ml of 1,4-dioxnae was used as a solvent, instead of 1.0 ml of mesitylene.

Experimental Example 1

Structure Analysis of an Organic Framework

1. IF Spectrum Comparison

Figure 5:
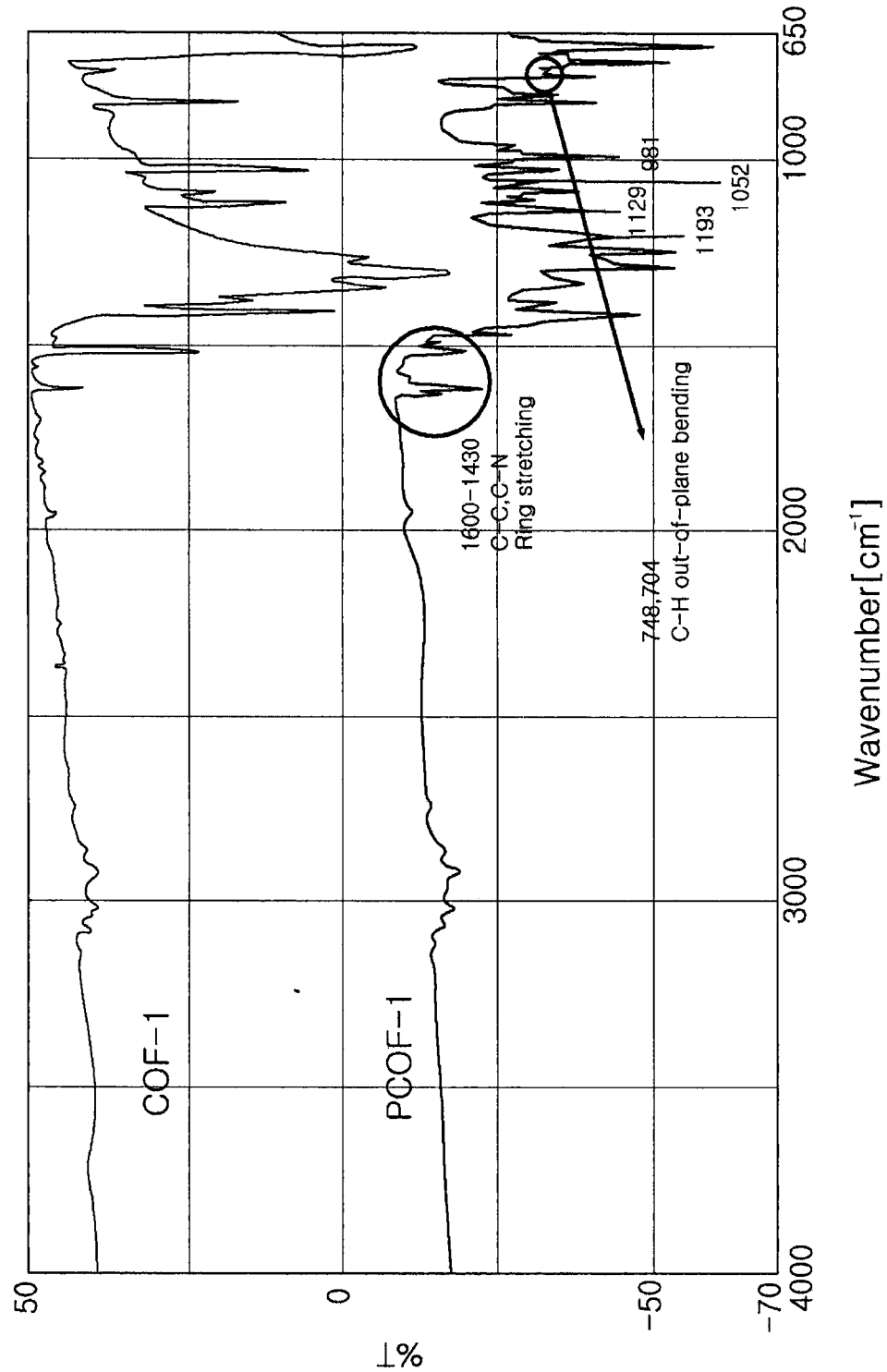
FIG. 5 shows infrared spectra of an organic framework (PCOF-1) prepared from Example 1, and a control group (COF-1).

In order to determine if a Lewis base is bonded to planar layers within the organic framework prepared from Example 1, infrared spectroscopy (IR) was used to analyze the spectrum of the organic framework (PCOF-1) prepared from Example 1. The results are shown in FIG. 5. Herein, as a control group, COF-1[$(C_3H_2BO)_6 \cdot (C_9H_{12})_1$] (Covalent Organic Framework-1, Science 2005, 310, 1166) was used.

Referring to FIG. 5, the organic framework (PCOF-1) of Example 1 shows a peak at 1600 to 1430 cm$^{-1}$, while the control group (COF-1) does not show a peak at around the abovementioned wave number. Herein, the peak at around the wave number (1600 to 1430 cm$^{-1}$) appears when C—C and C—N ring stretching exists. Also, it can be determined that in the organic framework (PCOF-1) of Example 1, peaks at 748 cm$^{-1}$ and 704 cm$^{-1}$ are assigned to C—H out-of-plane bending. This IR spectrum result indicates that in the organic framework (PCOF-1) of Example 1, pyridine is bonded to planar layers, unlike in a conventional organic framework (COF-1).

2. PXRD Pattern Comparison

Figure 7:
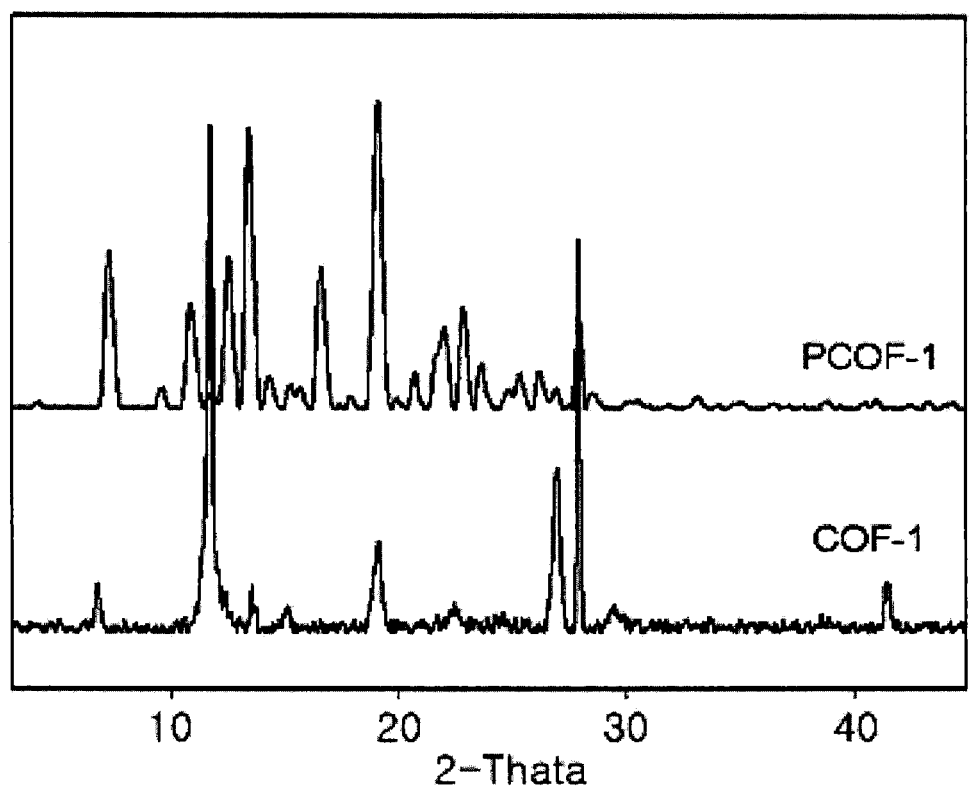
FIG. 7 shows graphs illustrating a powder x-ray diffraction (PXRD) analysis of an organic framework (PCOF-1) prepared from Example 1, and a control group (COF-1).

In order to determine if a Lewis base is bonded to planar layers in the organic framework (PCOF-1) prepared from Example 1, powder x-ray diffraction (PXRD) was carried out. The results are shown in FIG. 7. Herein, as a control group, COF-1 [$(C_3H_2BO)_6 \cdot (C_9H_{12})_1$] (Covalent Organic Framework-1, Science 2005, 310, 1166) was used.

As a result of the analysis, the organic framework (PCOF-1) of Example 1 showed the same characteristic peak as that of the control group (COF-1). From this, it can be found that the organic framework (PCOF-1) of Example 1 has a planar layer having the same structure as that of the conventional organic framework (COF-1). Meanwhile, the organic framework (PCOF-1) of Example 1 shows a peak, which is not shown in the conventional organic framework. Thus, from this peak, it can be speculated that a Lewis base is bonded to the planar layers.

Experimental Example 2

Thermal Property Analysis of an Organic Framework

Figure 6:
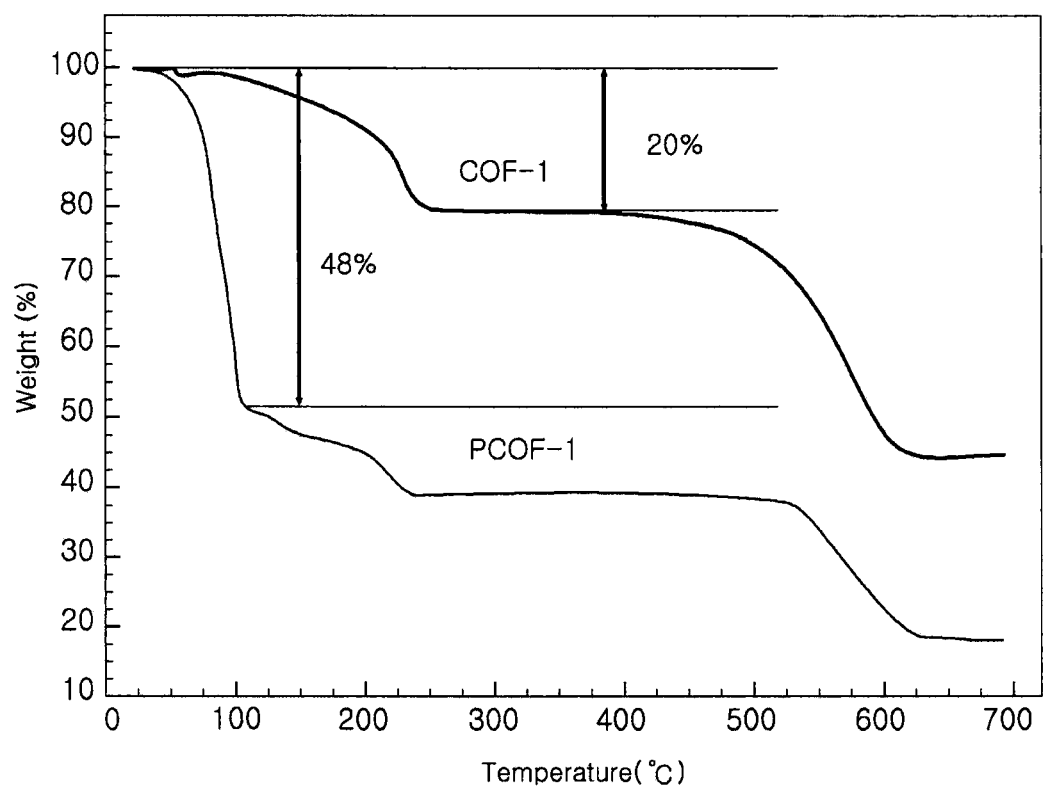
FIG. 6 shows graphs illustrating thermogravimetric analysis (TGA) of an organic framework (PCOF-1) prepared from Example 1, and a control group (COF-1).

In order to measure the thermal property of the organic framework (PCOF-1) prepared from Example 1, a thermogravimetric analysis (TGA) was carried out, and the results are shown in FIG. 6. Herein, as a control group, COF-1 [$(C_3H_2BO)_6 \cdot (C_9H_{12})_1$] (Covalent Organic Framework-1, Science 2005, 310, 1166) was used.

As shown in FIG. 6, the control group (COF-1) started to be thermally decomposed from a temperature of about 400° C., while the organic framework (PCOF-1) of Example 1 started to be thermally decomposed from a temperature of about 500° C. From these results, it was determined that the organic framework according to the present invention, which has a Lewis base coordinated to planar layers, has a thermal stability higher than a conventional two-dimensional planar organic framework.

Also, the control group (COF-1) showed a weight reduction of about 20% at a temperature of about 225° C., while the organic framework (PCOF-1) of Example 1 showed a weight reduction of about 48% at a temperature of about 100° C. Herein, the weight reduction was caused by evaporation of a solvent adsorbed on the organic framework by heating, the solvent having been used for synthesis of an organic framework. From the weight reduction rate caused by the evaporation of the solvent, it can be indirectly expected that the organic framework (PCOF-1) of Example 1 can adsorb guest molecules in a larger amount than the conventional organic framework (COF-1).

Experimental Example 3

Hydrogen Gas Adsorption Property of Organic Framework

Figure 8:
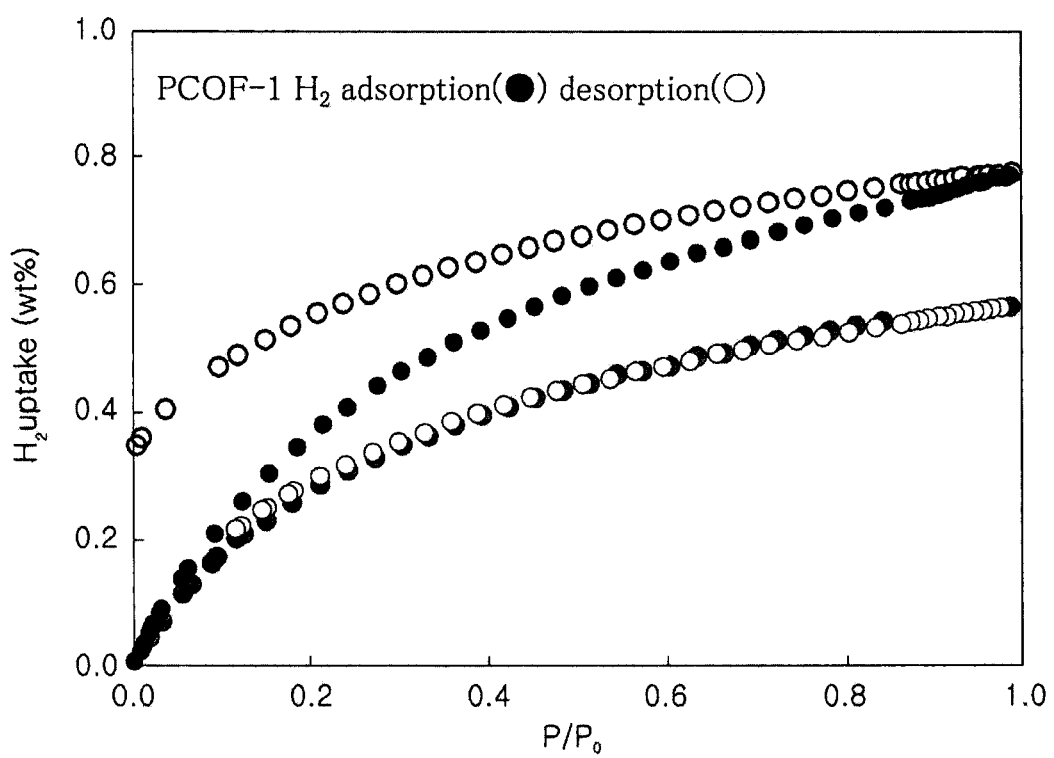
FIG. 8 shows graphs illustrating a hydrogen gas adsorption-desorption property of an organic framework (PCOF-1) prepared from Example 1, and a control group (COF-1).

In order to determine adsorption/desorption of hydrogen gas on/from the organic framework (PCOF-1) prepared from Example 1, automatic adsorption instrument was used to carry out a test on hydrogen gas adsorption at a temperature of 77K, and 1 atm, and the measurement results are shown in FIG. 8. Herein, as a control group, COF-1 [$(C_3H_2BO)_6 \cdot (C_9H_{12})_1$] (Covalent Organic Framework-1, *Science* 2005, 310, 1166) was used.

As a result of the test, as shown in FIG. 8, it can be seen that on the organic framework (PCOF-1) of Example 1, unlike on the control group (COF-1), hydrogen was irreversibly adsorbed.

Also, the hydrogen adsorption amount of the organic framework (PCOF-1) of Example 1 was about 0.75 wt % at $P/P_0=1.0$, while the hydrogen adsorption amount of the control group (COF-1) was about 0.55 wt % at $P/P_0=1.0$. This is because in the organic framework (PCOF-1) of Example 1, unlike in the control group (COF-1), pyridine as a Lewis base is introduced into the organic framework, thereby generating a new adsorption site. Herein, it is considered that the hydrogen adsorption amount was further increased because the generated adsorption site has high adsorption energy.

Experimental Example 4

Measurement on a Pore Size and an Interlayer Distance of an Organic Framework

In order to measure the distance between planar layers within the organic framework prepared from Example 1, a molecular modeling technique was used, and quantum mechanics calculation requiring no experimental parameter was introduced. A DMol$^3$ program of Materials Studio 4.3 package was used, and a combination of PBE/DNP was used to optimize the structure. Herein, the interlayer distance was set as a distance from a plane constituted by boron (B) atoms of one layer, to another plane constituted by boron (B) atoms of an adjacent layer. Specifically, in a hexagonal planar layer constituted by 6 random boron atoms, the coordinate of the center was calculated, and then a vertical distance from the point to the center coordinate of another adjacent hexagonal planar layer was calculated. As a result of the calculation, the interlayer distance was about 7.6 Å.

The invention claimed is:

1. An organic framework comprising:
    planar layers formed by successively connecting building blocks arranged in the vicinity of each other, in which each of the building blocks comprises two or three $C_6$ to $C_{204}$ aromatic ring groups covalently bonded to a linear or annular boron-containing cluster; and
    a Lewis base coordinated to the boron-containing cluster within the planar layers.

2. The organic framework as claimed in claim 1, wherein an interlayer distance between each of the planar layers and its adjacent planar layer ranges 4 to 15 Å.

3. The organic framework as claimed in claim 1, wherein the Lewis base is coordinated to a boron atom within the boron-containing cluster.

4. The organic framework as claimed in claim 1, wherein the Lewis base is coordinated to an atom within the boron-containing cluster in a vertical direction of the planar layers.

5. The organic framework as claimed in claim 1, wherein the boron-containing cluster comprises two atoms covalently bonded to a boron atom (B), selected from groups 15 and 16 of the Periodic Table, in which the two atoms are same or different.

6. The organic framework as claimed in claim 5, wherein each of the atoms covalently bonded to the boron atom is selected from the group consisting of nitrogen (N), oxygen (O), phosphorous (P), and sulfur (S).

7. The organic framework as claimed in claim 1, wherein the boron-containing cluster is represented by Formula 1 or 2 below:

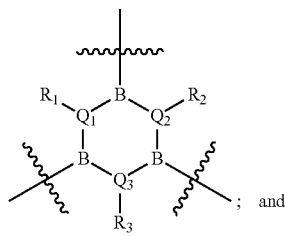

[Formula 1]

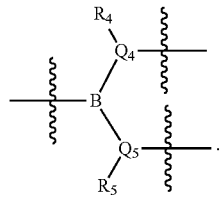

[Formula 2]

wherein, in Formulas 1 and 2, each of $Q_1$ to $Q_5$ independently represents an atom selected from groups 15 and 16 of the Periodic Table; each of $R_1$ to $R_5$ independently represents hydrogen, a $C_1$ to $C_{12}$ alkyl group, a $C_6$ to $C_{12}$ aryl group, or halogen; and provided that when at least one of $Q_1$ to $Q_5$ is an atom selected from group 16, at least one of $R_1$ to $R_5$ bonded to a corresponding atom of group 16 does not exist.

8. The organic framework as claimed in claim 1, wherein each of the $C_6$ to $C_{204}$ aromatic ring groups is represented by any one of Formulas 3 to 6 below:

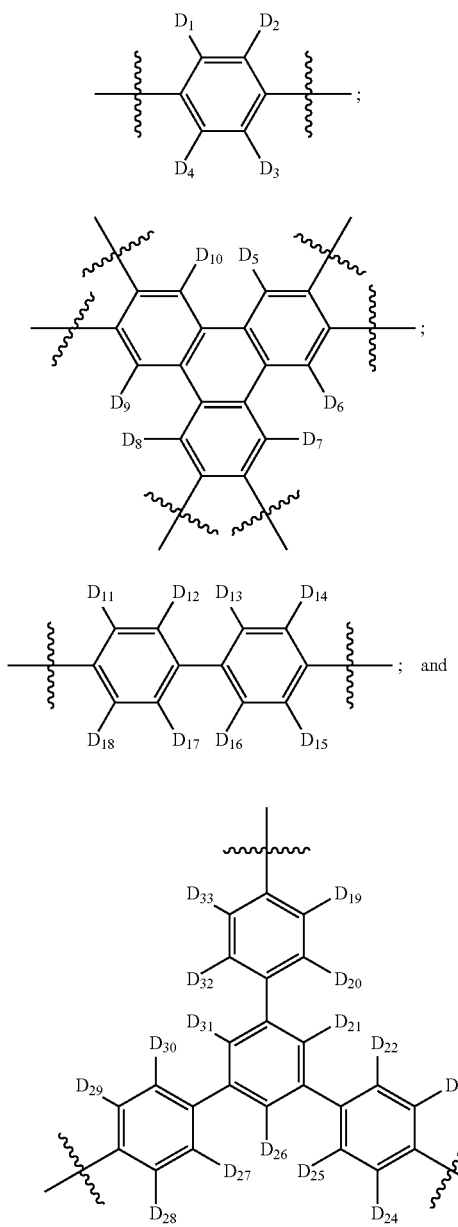

[Formula 3]

[Formula 4]

[Formula 5]

[Formula 6]

wherein in Formulas 3, 4, 5 and 6, each of $D_1$ to $D_{33}$ is independently selected from the group consisting of hydrogen, a $C_1$ to $C_{12}$ alkyl group, a $C_6$ to $C_{12}$ aryl group, and halogen.

9. The organic framework as claimed in claim 1, wherein each of the building blocks is represented by Formula 7 or 8 below:

[Formula 7]

[Formula 8]

wherein, in Formulas 7 and 8, $Q_1$ to $Q_5$, and $R_1$ to $R_5$ are the same as defined in claim 7; and $D_1$ to $D_{10}$ are the same as defined in claim 8.

10. The organic framework as claimed in claim 1, wherein each of the planar layers is represented by Formula 9 or 10 below:

[Formula 9]
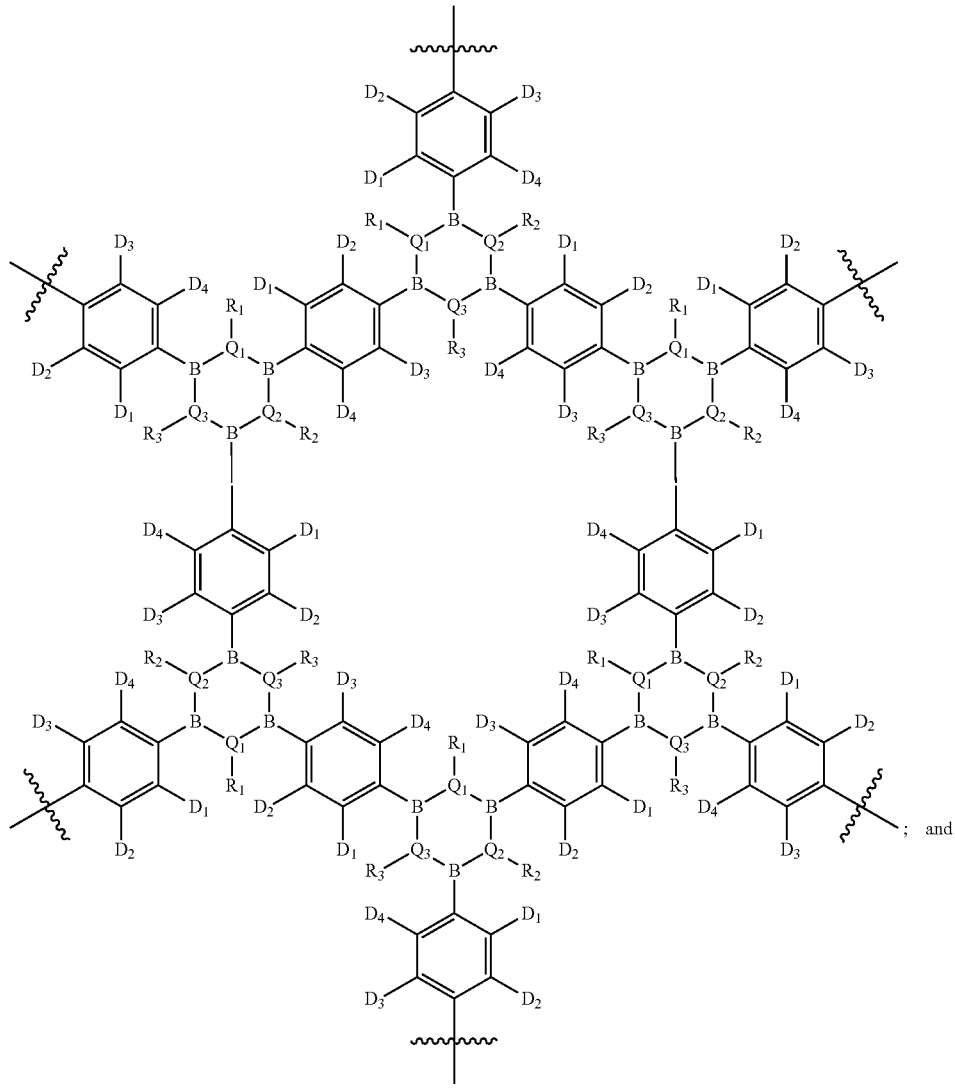
[Formula 10]
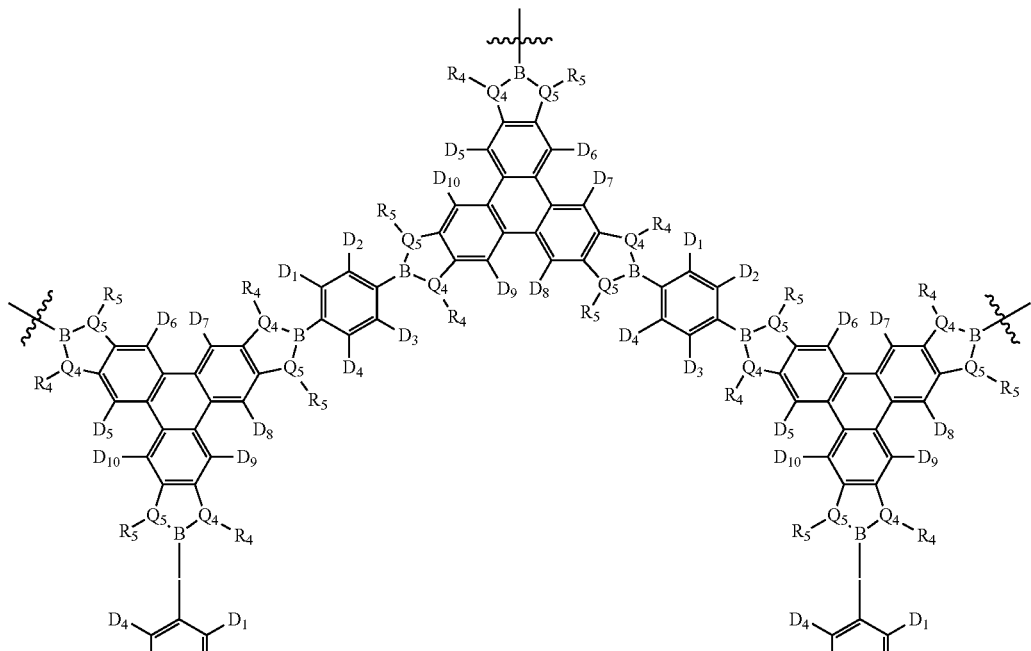

wherein, in Formulas 9 and 10, $Q_1$ to $Q_5$, and $R_1$ to $R_5$ are the same as defined in claim 7; and $D_1$ to $D_{10}$ are the same as defined in claim 8.

11. The organic framework as claimed in claim 1, wherein the Lewis base is a heterocyclic compound containing one or more selected from the group consisting of N, P, O and S.

12. The organic framework as claimed in claim 1, wherein the Lewis base is selected from the group consisting of pyridine, 4-cyanopyridine, 4-dialkylaminopyridine, 4,4'-bipyridine, pyrazine, pyridazine, pyrimidine, 2-methylpyrazine, pyrazol, imidazole, purine, 7-azaindole, quinoline, isoquinoline, quinoxaline, 1,4-diazabicyclo(2.2.2)octane, quinuclidine, 1,3,5-triazine, hexamethyleneteramine, piperidine, piperazine, pyrrolidine, morpholine, tetrahydrofuran, 1,4-dioxane and 1,8-naphthylene disulfide.

13. The organic framework as claimed in claim 1, which is prepared, in a presence of a solvent, by i) reacting a boron-containing compound represented by any one of Formulas 11, 12, and 13 below, with the Lewis base, or ii) reacting the boron-containing compound represented by any one of Formulas 11, 12, and 13 below, with aromatic polyalcohol and the Lewis base:

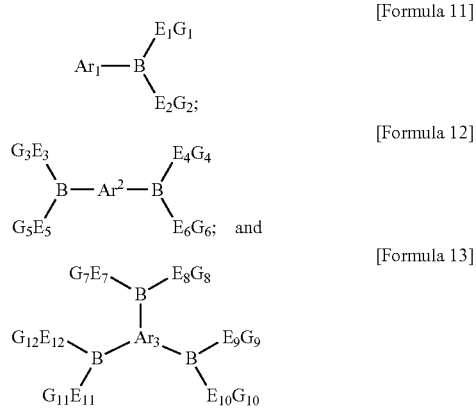

[Formula 11]

[Formula 12]

[Formula 13]

wherein, in Formulas 11, 12, and 13, $Ar_1$ represents a $C_6$ to $C_{204}$ aryl group, or a $C_6$ to $C_{204}$ heteroaryl group; $Ar_2$ represents a $C_6$ to $C_{204}$ arylene group or a $C_6$ to $C_{204}$ heteroarylene group; $Ar_3$ represents a $C_6$ to $C_{204}$ arenetriyl group or a $C_6$ to $C_{204}$ heteroarenetriyl group; each of $E_1$ to $E_{12}$ independently represents an atom selected from groups 15 and 16 of the Periodic Table; and each of $G_1$ to $G_{12}$ independently represents hydrogen, a $C_1$ to $C_{12}$ alkyl group, a $C_6$ to $C_{12}$ aryl group, or halogen.

14. The organic framework as claimed in claim 13, wherein the solvent is selected from the group consisting of mesitylene, 1,4-dioxane, and a mixture thereof.

15. The organic framework as claimed in claim 13, wherein the boron-containing compound is selected from the group consisting of benzene diboronic acid (BDBA), biphenyl-4,4'-diboronic acid (BPDA), tolane-4,4'-diboronic acid, stilbene-4,4'-diboronic acid, 1,3,5-benzenetriboronic acid (BTBA), 1,3,5-benzenetris(4-phenylboronic acid) (BTPA), 1,4-phenylenediboranediamine, and biphenyl-4,4'-diyldiboranediamine, and the aromatic polyalcohol is selected from the group consisting of hexahydroxy triphenylene, benzene-1,4-diol, and biphenyl-4,4'-diol.

16. The organic framework as claimed in claim 13, wherein a reaction temperature ranges from 40 to 160° C.

17. The organic framework as claimed in claim 1, which adsorbs and/or desorbs gas or organic molecules.

18. The organic framework as claimed in claim 17, which is a sensor, an isolate, a drying agent, an ion exchange material, a molecular sieve, a material for chromatography, a selective molecule releaser (or adsorbent), a molecule recognizing substance, a nanotube, or a nano reactor.

19. An adsorbent containing the organic framework as claimed in claim 1.

20. The adsorbent as claimed in claim 19, which adsorbs or stores an organic material, or gas selected from the group consisting of ammonia, carbon dioxide, carbon monoxide, hydrogen, amine, methane, oxygen, argon, and nitrogen.

21. A catalyst containing the organic framework as claimed in claim 1.

* * * * *